(12) United States Patent
Cosgrove et al.

(10) Patent No.: US 10,194,890 B2
(45) Date of Patent: Feb. 5, 2019

(54) BURR HOLE MOUNTED STEREOTACTIC BIOPSY DEVICE

(71) Applicant: Brown University, Providence, RI (US)

(72) Inventors: G. Rees Cosgrove, Providence, RI (US); Hannah Varner, Amherst, MA (US)

(73) Assignee: Brown University, Providence, RI (US)

( * ) Notice: Subject to any disclaimer, the term of this patent is extended or adjusted under 35 U.S.C. 154(b) by 529 days.

(21) Appl. No.: 14/525,995

(22) Filed: Oct. 28, 2014

(65) Prior Publication Data

US 2015/0119753 A1 Apr. 30, 2015

Related U.S. Application Data

(60) Provisional application No. 61/896,249, filed on Oct. 28, 2013.

(51) Int. Cl.
| | |
|---|---|
| *A61B 90/11* | (2016.01) |
| *A61B 10/04* | (2006.01) |
| *A61B 5/00* | (2006.01) |
| *A61B 90/10* | (2016.01) |
| *A61B 90/00* | (2016.01) |

(52) U.S. Cl.
CPC ............ *A61B 10/04* (2013.01); *A61B 5/4064* (2013.01); *A61B 90/11* (2016.02); *A61B 2090/103* (2016.02); *A61B 2090/3954* (2016.02); *A61B 2090/3966* (2016.02); *A61B 2090/3983* (2016.02)

(58) Field of Classification Search
CPC ............... A61L 90/11; A61L 2090/101; A61L 2090/103; A61L 2090/3954; A61L 2090/3966; A61L 2090/3983; A61L 5/4064; A61L 90/10; A61L 90/14; A61L 90/39; A61L 2090/363
See application file for complete search history.

(56) References Cited

U.S. PATENT DOCUMENTS

| | | | | |
|---|---|---|---|---|
| 6,328,748 | B1 * | 12/2001 | Hennig | A61B 17/3403 606/130 |
| 2002/0007187 | A1 * | 1/2002 | Amis | A61B 90/11 606/130 |
| 2002/0019641 | A1 * | 2/2002 | Truwit | A61B 90/11 606/130 |

(Continued)

*Primary Examiner* — Ryan J Severson
*Assistant Examiner* — Christian Knauss
(74) *Attorney, Agent, or Firm* — Adler Pollock & Sheehan P.C.; Daniel J. Holmander, Esq.

(57) ABSTRACT

A device for performing a biopsy on a brain is disclosed. The device includes a mount adapted for attachment to a burr hole on the skull of a patient. The mount has a body with a threaded surface and a cup-shaped surface forming a socket. The surface at the bottom of the socket defines a surgical aperture. A first arm extends away from the body, and has one fiducial marker. A second arm extends away from the body and has two spaced-apart fiducial markers. An instrument guide has a tubular body with a ball joint at one end with and an instrument insertion opening at an opposite end, configured to receive an instrument therethrough. The ball joint inserts into the socket, allowing the instrument guide to be positioned to a desired angle. A locking cup is attached to the body to secure the instrument in a fixed position.

10 Claims, 4 Drawing Sheets

(56) References Cited

U.S. PATENT DOCUMENTS

| | | | |
|---|---|---|---|
| 2002/0052610 A1* | 5/2002 | Skakoon | A61N 1/0534 606/129 |
| 2003/0055436 A1* | 3/2003 | Daum | A61B 90/11 606/130 |

* cited by examiner

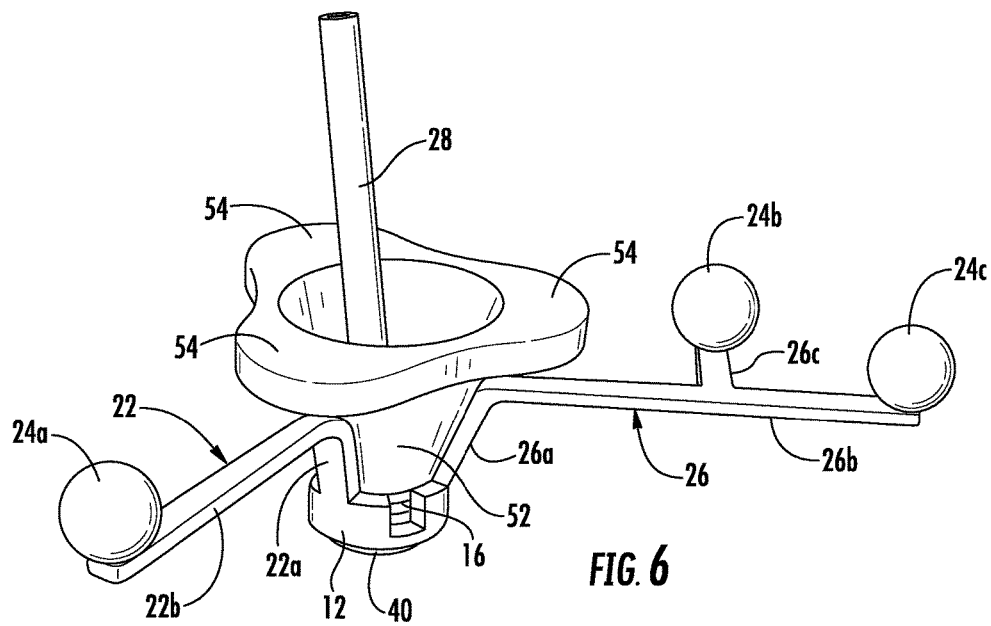
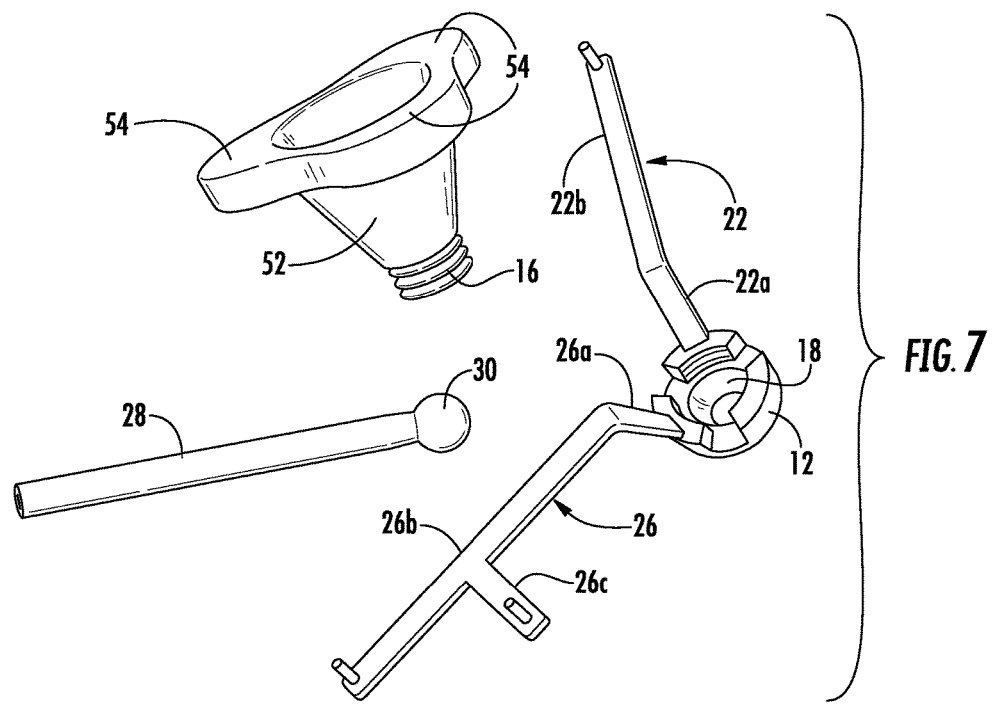

BURR HOLE MOUNTED STEREOTACTIC
BIOPSY DEVICE

CROSS-REFERENCE TO RELATED
APPLICATION

This application claims priority to earlier filed U.S. Provisional Application No. 61/896,249, filed Oct. 28, 2013, the contents of which are incorporated herein by reference.

BACKGROUND OF THE INVENTION

1. Field of the Invention

The present patent document relates generally to apparatuses for performing biopsies and more specifically to an apparatus and method to secure and guide a biopsy needle to a target within the brain.

2. Background of the Related Art

Stereotactic surgery utilizes the notion of a three dimensional coordinate system to assign coordinates to a target of interest. The most common method of stereotactic surgery utilizes a frame that is mounted to the patient's skull. The frame is registered on CT or MRI images and the relationship between the frame and target is used to adjust the coordinate system and perform a procedure. Modern imaging capabilities have enabled improved personalized medicine and advances in the precision of safely attaining targets within the patient's unique brain structure. In stereotactic surgery, markers on the patient are used as reference to extract the coordinates of a target and the frame may be 'set' to reach the specific location.

SUMMARY OF THE INVENTION

The device describe herein further utilizes modern technology to better target areas within the brain and streamline the process of biopsying lesions without the use of a frame. The vision is enabled by the use of an Image Guidance Systems ("IGS"). The IGS compiles scans of the patient with external markers (recognizable surface level features such as the face or separate fiducial markers placed on the patient) to produce a live updating three-dimensional image rendering of interior anatomy as the surgeon operates. Tool trajectories and hardware placement, for example, may be tracked and visualized on the screen.

Using an intra-operative CT and/or MRI scanner this device will utilize an IGS to target lesions within the brain for biopsy. The device will be skull-mounted at a standard 14 mm burr hole. Fiducial markers on the device will interface with the IGS. This device is unique from existing methods in that the fiducial markers are rigidly mounted to the patient's skull and eliminates the need for additional surgical arms and frames. The benefits of this approach of conventional frame-based biopsying include reduced scanning and fitting time necessitated by the use of a frame, increased relevance of the scans, shorter procedure times and intra-operative confirmation that the target has been achieved without clinical complications.

BRIEF DESCRIPTION OF THE DRAWINGS

These and other features, aspects, and advantages of the present invention will become better understood with reference to the following description, appended claims, and accompanying drawings where:

FIG. 6 is a left side perspective view thereof;
FIG. 7 is an exploded view thereof.

DESCRIPTION OF THE PREFERRED EMBODIMENT

Figure 1:
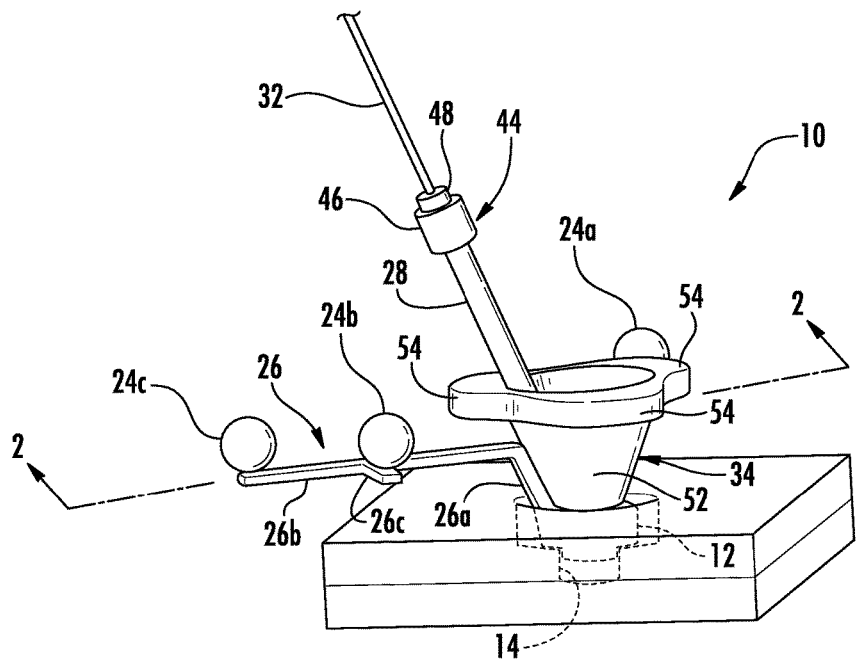
FIG. 1 is right side perspective view of the burr hole mounted stereotactic biopsy device.
Figure 2:
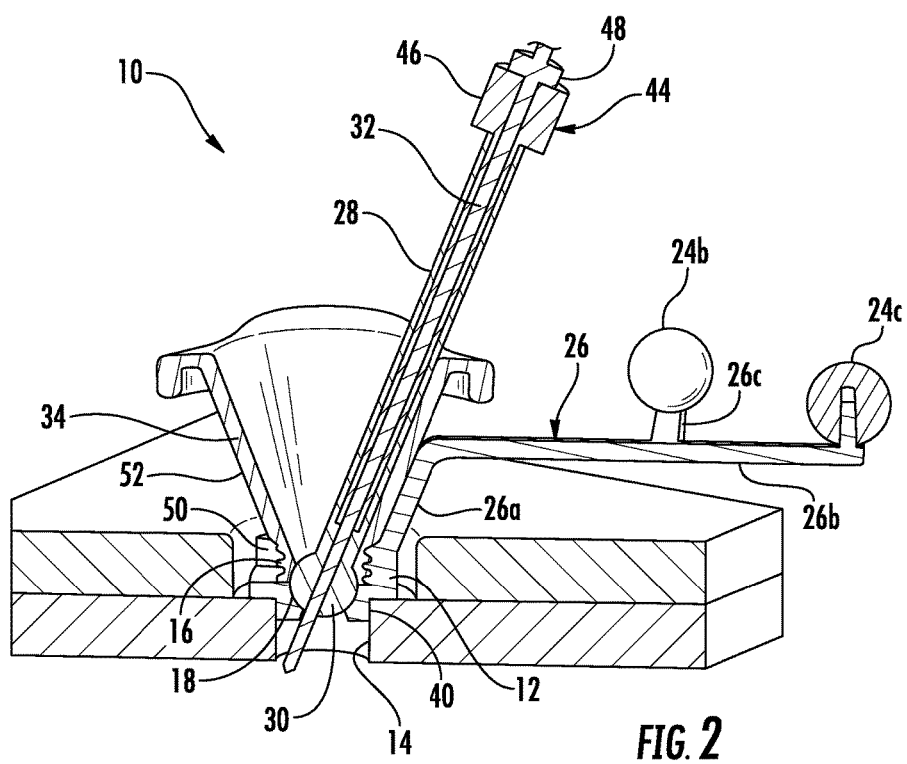
FIG. 2 is cross-section view through line 2-2 of FIG. 1.
Figure 3:
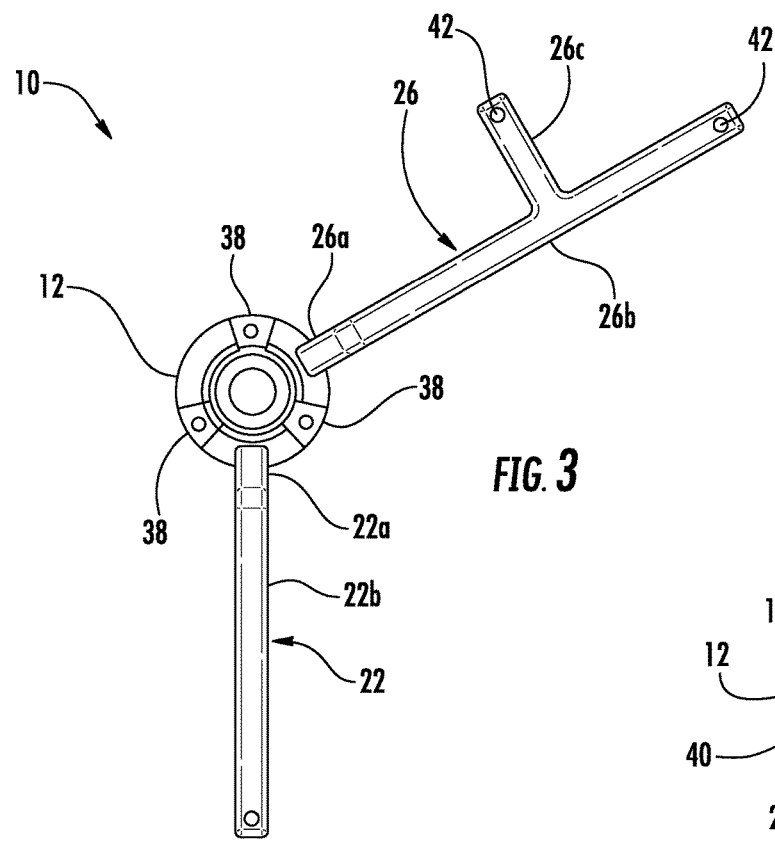
FIG. 3 is a top view thereof.
Figure 4:
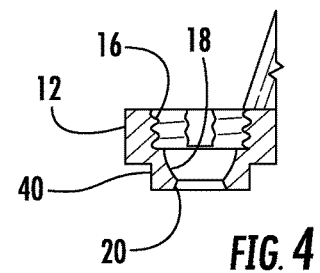
FIG. 4 is a partial cross-section view through line A-A of FIG. 3.
Figure 5:
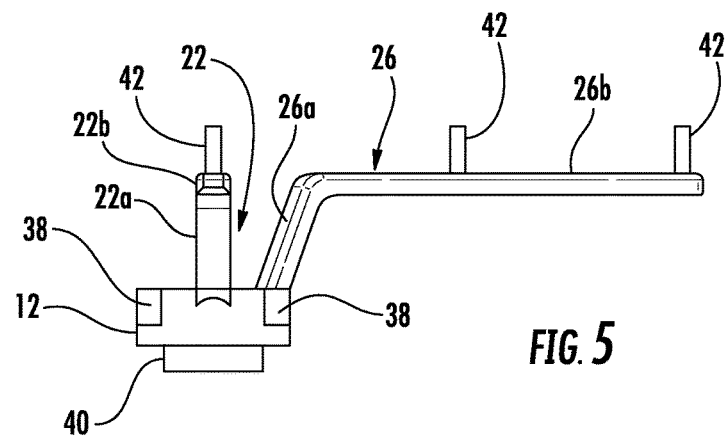
FIG. 5 is a front elevation view thereof.
Figure 8:
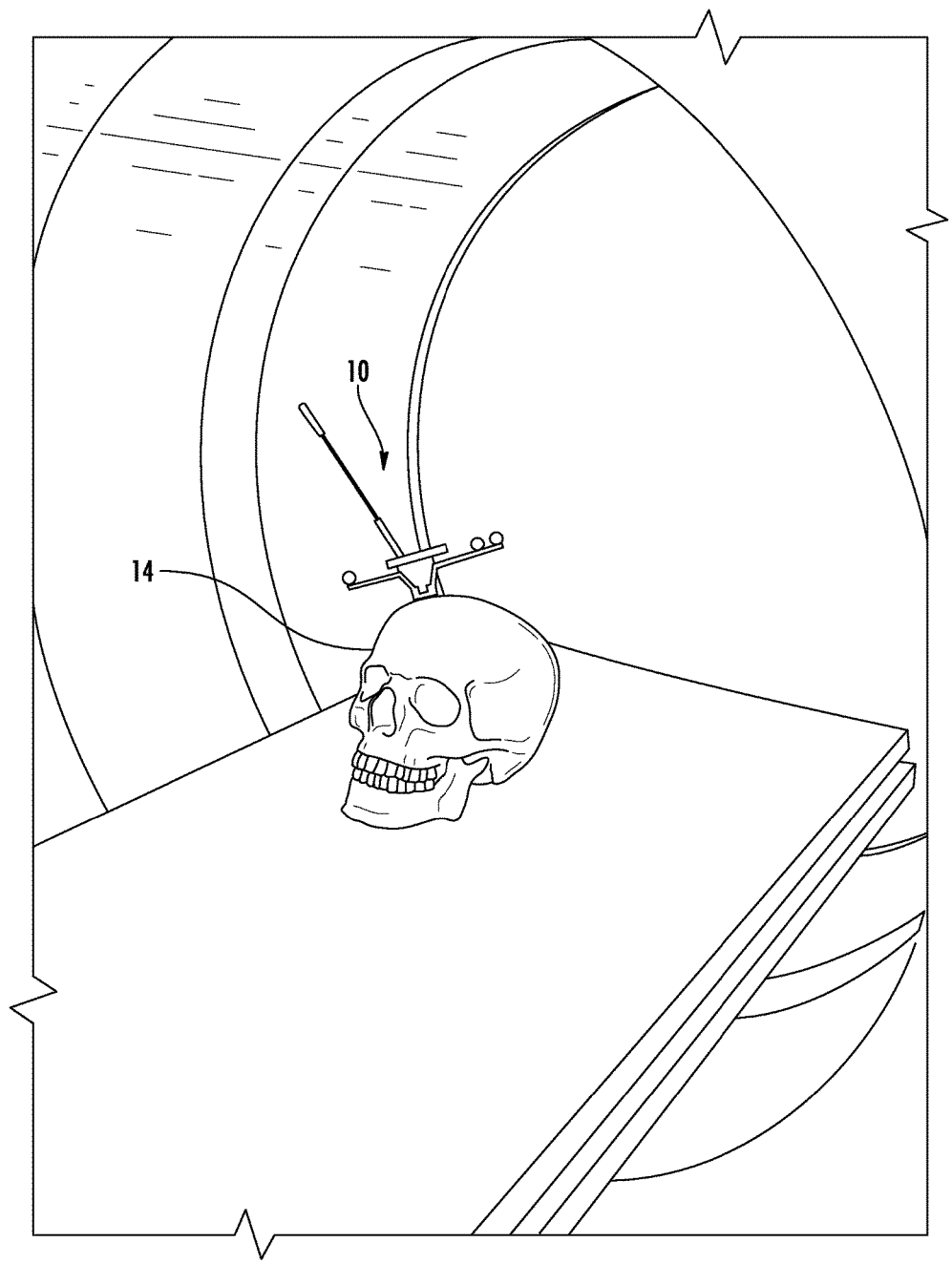
FIG. 8 is a perspective view of a burr hole mounted stereotactic biopsy device attached to a human skull, and placed inside a CT scanning machine.

Referring now to FIGS. 1-8, a stereotactic biopsy device for performing a biopsy on a brain is shown generally at 10. The mount 10 includes a body 12 adapted for attachment to a burr hole on a skull of a patient (exemplified at 14). The body 12 with a threaded surface 16 and a cup-shaped surface forming a socket 18. The surface at the bottom of the socket defines a surgical aperture 20. A first arm 22 extends away from the body 12, and has one fiducial marker 24a connected thereto. A second arm 26 extends away from the body 12 and has two spaced-apart fiducial markers 24b, 24c, connected thereto. An instrument guide 28 has a tubular body with a ball joint 30 at one end with and an instrument insertion opening at an opposite end, configured to receive an instrument 32 therethrough. The ball joint 30 inserts into the socket 18, allowing the instrument guide 28 to be positioned to a desired angle. A locking cup 34 is attached to the body 12 to secure the instrument 32 in a fixed position, whereby tightening the locking cup 34 secures the ball joint 30 of the instrument guide 28 in a fixed position on the skull for the biopsy.

Although the subject of the biopsy is typically a human patient undergoing a brain biopsy procedure, this device and procedure could be used on other animal brains as well other procedures where an instrument must be inserted into the brain to deliver treatment to a surgical site within the brain.

The body 12 may be generally ring-shaped. The body 12 may further include attachment points 38, such as apertures, formed through the body 12 to secure the mount 10 to the skull via fasteners. The mount 10 may further include an annular wall 40 depending downwardly from the body 12, sized and dimensioned to insert into the burr formed in the skull. The annular wall 40 may have a diameter of fourteen millimeters. The annular wall 40, in addition to the fasteners, would eliminate lateral movement of the mount 10 on the skull.

The first arm 22 and the second arm 26 may each include a first portion 22a, 26a that extends at about 68° upwardly and away from the body 12 and a second portion 22b, 26b extending parallel to the body 12, thereby elevating the first arm 22 and second arm 26 away from the skull, permitting the mount 10 to be flexibly positioned without undue interference from the first arm 22 or second arm 26.

The first arm 22 and the second arm 26 may be offset at a 120° angle from each other. The first arm 22 includes a fiducial marker 24a located at a distal end of the first arm 22. The second arm 26 includes a branch 26c extending perpendicular to the second arm 26, thereby forming a semi-y-shape. Fiducial markers 24b, 24c are at a distal end of the branch 26c and at a distal end of the second arm 26. Between the three fiducial markers 24a, 24b, 24c on both arms 22, 26, each at known distance from one another, the exact topography of the brain may be calculated with image guidance systems using CT and/or MRI machines. Optionally, the first arm 22 may also include a branch with a fourth fiducial marker (not shown), providing an added reference point for added triangulation precision. The fiducial markers 24a, 24b, 24c may be mounted to the first arm 22 and the second arm 26 via posts 42.

The fiducial markers 24a, 24b, 24c are manufactured from a proprietary material designed to be visible to medical imaging systems, such as CT and/or MRI machines.

A reducing tube 44 may be included, which is configured and arranged to insert into the tubular body of the instrument guide 28, the reducing tube 44 has a channel adapted for insertion of an instrument 32 therethrough that is sized to match the desired instrument. The reducing tube 44 further has an enlarged end 46 configured and arranged to abut the insertion opening of the instrument guide 28. In practice, a number of different sized reducing tubes 44 are available during a surgery for each of the desired instrument 32 to be used, which may have different diameters.

A depth stopper 48 may be provided for each instrument 32 to prevent the instrument 32 from being inserted too far into the instrument guide 28 and, consequently, the brain, thereby preventing accidental injury to the patient.

The locking cup 34 has a threaded end 50 adapted to attach to the threaded surface 16 of the body 12. The locking cup 34 may further include conical body portion 52 extending upwardly from the threaded end 52. The locking cup 34 may further include three spaced-apart lobes 54 extending radially from an end of the conical body portion 52, providing a gripping surface for the surgeon to tighten the locking cup 34. An optional chuck (not shown) adapted to interlock with the lobes 54 of the locking cup 34, may be used to provide the surgeon with added torque when tightening the locking cup 34 onto the body 12.

In use, the surgeon who performs the stereotactic biopsy on the brain forms a burr hole in a skull 14 of the subject of the biopsy, typically 14 mm in diameter. The surgeon then attaches the mount 10 to the burr hole, typically via fasteners. The surgeon then secures an instrument guide 28 to the mount 10 and aligns the instrument 32 to the desired angle of approach to the surgical site within the brain. The desired angle of approach is determined typically using medical imaging of the skull via CT and/or MRI scanning. The surgeon may then secure the instrument guide 28 to the mount 10 by tightening the locking cup 34 onto the mount 10, thereby crimping the ball joint 30 of the instrument guide 28 in position on the socket 18 of the mount 10.

The surgeon may select and insert the desired reducing tube 44 into the instrument guide 28 based on the desired instrument 32 to be used in the surgery. As noted earlier, the surgeon may attach a depth stopper 48 to the instrument 32 prior to inserting the instrument 32 into the instrument guide 28. The surgeon may then insert an instrument 32 into the instrument guide 28 and manipulate the instrument 32 to perform the surgery, such as a biopsy.

Therefore, it can be seen that the present invention provides a unique solution to the problem of conducting a stereotactic biopsy on the brain which reduces scanning and fitting time necessitated by the use of a frame, increases relevance of the scans, shortens procedure times and intra-operative confirmation that the target has been achieved without clinical complications to the patient.

It would be appreciated by those skilled in the art that various changes and modifications can be made to the illustrated embodiments without departing from the spirit of the present invention. All such modifications and changes are intended to be within the scope of the present invention except as limited by the scope of the appended claims.

What is claimed is:

1. A stereotactic biopsy device for performing a biopsy on a brain, comprising:
   a mount adapted for attachment to a burr hole on a skull of a subject of a biopsy, said mount having a body with a threaded surface and a cup-shaped surface forming a socket, a surface at a bottom of the socket defining a surgical aperture therethrough;
   a first arm extending away from the mount having at least one fiducial marker attached thereto, the first arm includes a first portion extending at about 68° upwardly and away from the body and a second portion extending parallel to the body;
   a second arm comprising a first portion extending upwardly and away from the body and a second portion extending parallel to the body, the second arm further comprising a branch extending from the second portion and perpendicular thereto, the second arm having one fiducial marker at a distal end of the branch and a second fiducial marker at a distal end of the second portion of the arm;
   an instrument guide having a tubular body with a ball joint at one end with and an instrument insertion opening at an opposite end in fluid connection, the tubular body configured and arranged to receive an instrument therethrough, guiding the instrument through the surgical aperture, the ball joint configured and arranged to insert into the socket on the body, the instrument guide positionable within the socket via the ball joint at a desired angle of approach; and
   a locking cup having a threaded end adapted to secure to the threaded surface of the body;
   whereby tightening the locking cup secures the ball joint of the instrument in a fixed position for the biopsy.

2. The device of claim 1 wherein the first arm has one fiducial marker at a distal end of thereof.

3. The device of claim 1, wherein the first arm is offset at a 120° angle from the second arm.

4. The device of claim 1, wherein the first portion of the second arm extends at about 68° upwardly and away from the body.

5. The device of claim 1, further comprising a reducing tube configured and arranged to insert into the tubular body of the instrument guide, the reducing tube having a channel adapted for insertion of an instrument therethrough, the reducing tube further having an enlarged end configured and arranged to abut the insertion opening.

6. The device of claim 1, wherein the locking cup comprises a conical body portion extending upwardly from the threaded end.

7. The device of claim 6, wherein the locking cup further comprises three space-apart lobes extending outwardly from an end of the conical body portion.

8. The device of claim 1, wherein the mount further comprises an annular wall depending downwardly from the body, sized and dimensioned to insert into the burr hole formed in the skull.

9. The device of claim 8, wherein the annular wall has a diameter of fourteen millimeters.

10. The device of claim 1, further comprising attachment points formed in the body configured and arranged to secure the body to the skull via fasteners.

* * * * *